United States Patent [19]

Brennan et al.

[11] 4,239,927
[45] Dec. 16, 1980

[54] REMOVAL OF ORGANIC CHLORIDES FROM SYNTHETIC OILS

[75] Inventors: James A. Brennan, Cherry Hill; Henry D. Norris, Woodbury, both of N.J.

[73] Assignee: Mobil Oil Corporation, New York, N.Y.

[21] Appl. No.: 27,226

[22] Filed: Apr. 5, 1979

[51] Int. Cl.³ .......................................... C07C 15/107
[52] U.S. Cl. ...................................... 585/24; 585/313; 585/323; 585/329; 585/532
[58] Field of Search ................. 585/24, 323, 455, 456, 585/532, 329, 312, 313

[56] References Cited

U.S. PATENT DOCUMENTS

| | | | |
|---|---|---|---|
| 2,506,551 | 5/1950 | Sachanen et al. | 585/446 |
| 3,173,965 | 3/1965 | Pappas et al. | 585/24 |
| 3,600,451 | 8/1971 | Rowe | 585/532 |
| 3,725,498 | 4/1973 | Brennan | 585/532 |
| 3,833,678 | 9/1974 | Brennan | 585/532 |
| 4,035,308 | 7/1977 | Schenach | 585/24 |

*Primary Examiner*—Curtis R. Davis
*Attorney, Agent, or Firm*—Charles A. Huggett; Raymond W. Barclay; Claude E. Setliff

[57] ABSTRACT

In producing synthetic hydrocarbon oils by polymerization of olefins using aluminum halide as the catalyst, organic halides are produced. These are corrosive to metal equipment and are poisonous to certain hydrogenation catalysts. This invention is concerned with reacting such organic halides with an aromatic hydrocarbon in a system also containing the polyolefins thus forming an alkylation product with both reactants prior to removal of the aluminum chloride catalyst.

14 Claims, No Drawings

REMOVAL OF ORGANIC CHLORIDES FROM SYNTHETIC OILS

BACKGROUND OF THE INVENTION

1. Field of the Invention

The invention is concerned with the production of synthetic lubricating oils. More particularly, it is concerned with the reaction of an aromatic hydrocarbon with an olefin-organic halide reaction mixture.

2. Discussion of the Prior Art

It is well known in the art that aluminum halides, especialy aluminum chloride and bromide, are useful catalysts for certain hydrocarbon reactions, including polymerization and isomerization. U.S. Pat. No. 3,725,498 teaches an improved liquid aluminum halide catalyst, wherein the halide is dissolved in an ester containing at least 5 carbon atoms, for use as catalyst for olefin polymerization. The solution is capable of dissolving more than a 1:1 mole solution of complex at temperatures above 30° to 50° C., thus making it possible to maintain desired proportions of catalyst and olefin. U.S. Pat. No. 3,600,451 also teaches alkylation using polyisobutylene.

The present invention, as will become apparent from the remaining disclosure, is concerned with the discovery of a way to make an effective lubricating oil without having to remove the polymerization catalyst or even to hydrogenate the polyolefin.

SUMMARY OF THE INVENTION

In accordance with the invention there is provided a process for making an oil of lubricating viscosity by the steps comprising:

(1) reacting a $C_8$-$C_{10}$ olefin in the presence of an aluminum halide catalyst to give a polymer containing from 20 to 150 carbon atoms, preferably 30 to 100 carbon atoms, and, without removing the aluminum halide, (2) contacting the total reaction mixture from (1) with a monocyclic aromatic compound, e.g. benzene.

The invention also includes the product of such reaction.

DESCRIPTION OF SPECIFIC EMBODIMENTS

There are at least two serious problems associated with the use of either solid aluminum halides or the above-mentioned liquid catalyst system. These are that the product prior to hydrogenation has an unacceptably high metal corrosion rate and it deactivates a portion of the hydrogenation catalyst used following the polymerization. These problems have greatly affected the manufacturing cost of synthetic stocks, which are becoming more and more valuable as base stock for synthetic industrial and automotive oils. For example, deactivation of the hydrogenation catalyst alone accounts for a considerable increase in cost. The cause of the problems has been an elusive one, and has led to a considerable amount of research.

One of the unexpected advantages of the method of this invention was the discovery that the product obtained was in every respect equal in value to the hydrogenated polyolefin as a lubricant. It was surprising to find that the products of the present method have virtually the same viscosity, the same stability, similar lubricity properties, and the like.

In the discussion which follows, the expression "aluminum halide", or simply "halide", will be understood to include any of the useful olefin polymerization catalysts, and especially include aluminum chloride or bromide.

The catalyst used in the present invention may be solid aluminum halide or a solution or complex of an aluminum halide, such as the chloride or bromide, dissolved in an ester, the solution or complex containing more than one mole of the halide per mole of ester. In general, the amount of, for example, aluminum halide dissolved per mole of ester will be between about 1.1 moles and about 1.4 moles. A 1.1 mole solution has little or no catalytic activity. The aluminum halide in excess of one mole in the solution appears to be the component that imparts catalytic activity to the catalyst solution. Thus, the amount of solution employed to catalyze the reaction will be governed only by the need to provide sufficient excess of aluminum halide to catalyze the olefin polymerization reaction that is ordinarily catalyzed by solid aluminum halide.

The solution of aluminum halide in ester is formed readily. A 1:1 mole solution or complex readily forms at room temperature and this solution is capable of dissolving additional aluminum halide at temperatures of 30°-50° C. In order to avoid hydrolysis due to moisture, it is preferred to prepare the catalyst solution in a dry, inert atmosphere, such as nitrogen or dry air.

The solvent ester, in accordance with this invention, is the methyl ester of certain alkanoic acids. The esters contemplated include methyl esters of such acids as n-butyric, n-valeric, n-hexanoic, isovaleric, trimethylacetic, 2-methylvaleric, 2-ethylbutyric, and 2-ethylhexanoic acids.

Of particular interest in connection with the present invention is the continuous polymerization, with catalyst recycle, of olefins to liquid polymers useful as synthetic lubricants. A wide variety of olefins can be polymerized with the stable catalyst solution. However, this invention is concerned with those containing only 8 to 10 carbon atoms, i.e. octene, nonene and decene, and mixtures thereof. They can be straight chain or branched chain. Although preferred among these are the 1-olefins, those having internal double bonds are contemplated. Furthermore, the olefin reactant can be a single olefin or a mixture of olefins, of which the following are non-limiting examples: octene-1; octene-1; octene-2; 2-ethylhexene-1; nonene-1; nonene-2; decene-1; and decene-2.

The polymerization of the olefin is carried out at temperatures of between about 0° C. and about 100° C. for a period of time of about 1-3 hours. Ordinarily it is carried out at substantially atmospheric pressure, but, particularly with lower olefins, superatmospheric pressures sufficient to maintain liquid phase can be advantageously employed. The amount of catalyst employed will generally be about 0.1 to about 5 percent, by weight of olefin, based on excess aluminum halide, e.g., the chloride. In some operations, in order to render polymer products less viscous and more readily handled, a solvent inert to the polymerization can be used. Suitable solvents include kerosene and paraffins, such as heptane, octane, isooctane, decane, and the like.

Because the catalyst solution is a heavy liquid, when its removal is desired the effluent from the reactor is permitted to stand quietly until the major amount of the catalyst solution has separated as a lower heavy layer. Alternatively a centrifuge may be used to speed the separation. This layer is recycled, after reconstitution, with fresh aluminum chloride, as needed. Then, the remaining polymer product can be washed free of any residual catalyst solution, dried and freed of solvent and monomer by distillation. The preparation of the catalyst is fully described in U.S. Pat. No. 3,833,678, which is incorporated herein by reference.

We have discovered that both problems mentioned hereinabove are related to organic halides formed during the polymerization reaction in the presence of trace amounts of water. The water, it is believed, reacts with, for example, aluminum chloride, to form hydrogen chloride and complex aluminum oxychloride compounds. The aluminum chloride then catalyzes the addition of hydrogen chloride to an olefin. These reactions may be shown as follows:

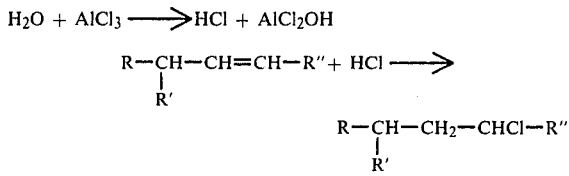

wherein R, R' and R" may be straight or branched hydrocarbyl groups or hydrogen.

The organic halides formed are of variable stability and some decompose on heating with liberation of hydrogen halide. This has led to corrosion in the distillation section of the plant, and is attributed to the combination of the liberated hydrogen halide with trace amounts of water in the cooler sections of the recovery system.

Organic halides which survive the distillation are carried into the hydrogenation vessel and are catalytically dehydrohalogenated. The hydrogen halide formed reacts with and deactivates the hydrogenation catalyst, e.g., a nickel catalyst.

In accordance with this invention, both problems of corrosion and hydrogenation catalyst deactivation are solved by reacting a monocyclic aromatic compound, including benzene, toluene (methylbenzene) and the xylenes (dimethylbenzenes), with the polymerized mixture prior to removal of the aluminum halide catalyst to scavenge the organic halide by alkylation of the aromatic compound. The monocylic aromatics used in this invetion may contain from 0 to 2 $C_1$-$C_{10}$ hydrocarbyl substituents. Obviously, when no substituent is present, the aromatic is benzene. Other hydrocarbyl groups that may be attached include ethyl, butyl, octyl and decyl.

The alkylation reaction is generally carried out at from about 80° to about 100° C. and requires varying times of from about 1 to about 3 hours. While an amount of aromatic compound equivalent to the polymer and organic halide in the reaction mixture formed may be used, we prefer to use an excess of aromatic compound corresponding to from about 5 to about 10 times the amount of polymer plus organic halide present.

While any method for alkylation that reasonably occurs to one of skill in this art might be used, we prefer, in commercial operations, to add the reaction mixture as obtained, and which still contains the aluminum halide catalyst, to a hot aromatic compound. This is true although the illustrations which follow involve adding benzene to the mixture.

The reaction during alkylation is shown below, illustrated with benzene.

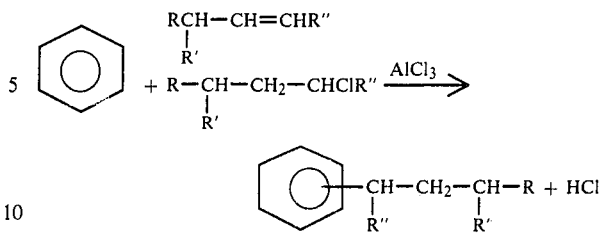

Having described the invention in general terms the following is offered as specific illustrations. It will be understood that they are illustrative only.

EXAMPLE 1

The catalyst was prepared by dissolving anhydrous aluminum chloride in methyl-n-butyrate at room temperature, in a molar proportion, respectively, of 1.31:1.

This catalyst and 1-decene were metered at 38 g./hr. and 552 g./hr., respectively, over a two-hour period into a reaction vessel fitted with stirrer, thermometer and reflux condenser. The mixture was stirred and maintained at 45° C. After addition of the catalyst and 1-decene was complete, the mixture was maintained at 45° C. for an additional 15 minutes. 1000 ml. of benzene was then added and the mixture was stirred at reflux (85°–88° C.) for 2.5 hours, after which the reaction mixture was quenched with 250 ml. of 8% aqueous HCl, was made basic with dilute $NH_4OH$ and was washed out with water until neutral. Benzene, olefin monomer and dimer were removed by distillation, the monomer at 80° C. and 60 mm. of pressure and the dimer at 120° C. and 1 mm. of pressure. The yield of oil, based on olefin, was 95%. The oil had a number average molecular weight of about 1400, a viscosity of 521 cs. at 100° F. and contained only 5 ppm. of chlorine. Infra red spectra of the oil showed the presence of aromatic rings with only a trace of olefin.

EXAMPLE 2

A polymerization followed by alkylation identical to Example 1 was done, except that 940 g. of 15/85 octene/decene was substituted for the decene, the addition time was shortened to one hour and 42 minutes and a 150 ml. portion of the reaction mixture was withdrawn at the end of the 15 min. hold period prior to the addition of the benzene.

The 150 ml. portion and the main reaction product were worked up separately as above, i.e., contacted with HCl, etc. From the 150 ml. portion there was obtained a 99% yield of an oil with a viscosity of 38.2 cs. and 400 cs. at 210° F. and 100° F., respectively. The oil contained 174 ppm. of chlorine.

The alkylation product, obtained in >93% yield, had a number average molecular weight of 1467, a viscosity of 46.4 cs. at 210° F. and 550 cs. at 100° F. and contained <1 ppm. of chlorine.

EXAMPLE 3

A polymerization and an alkylation reaction were performed as in Example 1, except that 867 g. of toulene was substituted for the benzene and the mixture was heated to 85° C. and held at this temperature for 2.5 hours. After work-up (as above) the oil (95% yield) had a viscosity of 43.6 cs. at 210° F. and 529 cs. at 100° F. and contained 4 ppm. of chlorine.

It should be noted, as candor requires, that it is well known that aluminum halide will catalyze the alkylation of an aromatic compound with an alkyl halide. This fact is stated in U.S. Pat. No. 2,506,551, but there is nothing in the patent, or in any other reference known to applicants, which would suggest the discovery of the problem in their polymerization process that the total mixture, polymer as well as organic halide, could be reacted with a monocyclic aromatic compound to give a product as useful for its lubricating properties as the product obtained by hydrogenation of the polyolefin. Nor is any art known which would suggest that the instantly disclosed alkylation reacation would take place in the complex system of the claimed process, or that would suggest the product from such process.

We claim:

1. A process for making an oil of lubricating viscosity by the steps comprising:
   (1) reacting a $C_8$–$C_{10}$ olefin in the presence of an aluminum halide catalyst to give a polymer containing from 20 to 150 carbon atoms, preferably 30 to 100 carbon atoms, and, without removing the aluminum halide,
   (2) contacting the total reaction mixture from
      (1) with a monocyclic aromatic compound.
2. The process of claim 1 wherein the aromatic compound contains up to 2 $C_1$–$C_{10}$ hydrocarbyl groups.
3. The process of claim 1 wherein said olefin is 1-decene.
4. The process of claim 1 wherein said olefin is a mixture of octene and decene.
5. The process of claim 4 wherein said mixture contains 15% by weight of octene and 85% by weight of decene.
6. The process of claim 2 wherein said aromatic compound is benzene.
7. The process of claim 2 wherein said aromatic compound is toluene.
8. A product obtained by the steps comprising:
   (1) reacting a $C_8$–$C_{10}$ olefin in the presence of an aluminum halide catalyst to give a polymer containing from 20 to 150 carbon atoms, preferably 30 to 100 carbon atoms, and, without removing the aluminum halide,
   (2) contacting the total reaction mixture from
      (1) with a monocyclic aromatic compound.
9. The product of claim 8 wherein the aromatic compound contains up to 2 $C_1$–$C_{10}$ hydrocarbyl groups.
10. The product of claim 8 wherein said olefin is 1-decene.
11. The product of claim 8 wherein said olefin is a mixture of octene and decene.
12. The product of claim 11 wherein said mixture contains 15% by weight of octene and 85% by weight of decene.
13. The product of claim 9 wherein said aromatic compound is benzene.
14. The product of claim 9 wherein said aromatic compound is toluene.

* * * * *

UNITED STATES PATENT AND TRADEMARK OFFICE
CERTIFICATE OF CORRECTION

PATENT NO. : 4,239,927
DATED : December 16, 1980
INVENTOR(S) : James A. BRENNAN and Henry D. MORRIS It is certified that error appears in the above-identified patent and that said Letters Patent are hereby corrected as shown below:

Column 2, line 10, "1.1" should read "1:1".

Column 2, line 45, "octene-1;" occurs twice; delete one occurrence

Column 5, line 13, "reacation" should read "reaction".

Signed and Sealed this

Tenth Day of March 1981

[SEAL]

Attest:

RENE D. TEGTMEYER

*Attesting Officer*   *Acting Commissioner of Patents and Trademarks*